(12) United States Patent
Conn

(10) Patent No.: US 9,068,989 B2
(45) Date of Patent: Jun. 30, 2015

(54) REAGENT SYSTEM AND METHOD

(75) Inventor: Costa Conn, Dulwich Hill (AU)

(73) Assignee: LEICA BIOSYSTEMS MELBOURNE PTY LTD, Victoria (AU)

( * ) Notice: Subject to any disclaimer, the term of this patent is extended or adjusted under 35 U.S.C. 154(b) by 482 days.

(21) Appl. No.: 13/387,289

(22) PCT Filed: Jul. 29, 2010

(86) PCT No.: PCT/AU2010/000956
§ 371 (c)(1),
(2), (4) Date: Apr. 12, 2012

(87) PCT Pub. No.: WO2011/011826
PCT Pub. Date: Feb. 3, 2011

(65) Prior Publication Data
US 2012/0208287 A1 Aug. 16, 2012

Related U.S. Application Data

(60) Provisional application No. 61/229,644, filed on Jul. 29, 2009.

(30) Foreign Application Priority Data

Jul. 29, 2009 (AU) ................................ 2009903535

(51) Int. Cl.
| | |
|---|---|
| *G01N 21/00* | (2006.01) |
| *G01N 33/58* | (2006.01) |
| *C07C 245/10* | (2006.01) |
| *C07F 9/12* | (2006.01) |
| *G01N 1/30* | (2006.01) |
| *G01N 33/535* | (2006.01) |
| *C12Q 1/42* | (2006.01) |

(52) U.S. Cl.
CPC ............ *G01N 33/581* (2013.01); *C07C 245/10* (2013.01); *C07F 9/12* (2013.01); *C12Q 2334/70* (2013.01); *G01N 1/30* (2013.01); *G01N 33/535* (2013.01); *C12Q 1/42* (2013.01)

(58) Field of Classification Search
None
See application file for complete search history.

(56) References Cited

U.S. PATENT DOCUMENTS 5,480,791 A 1/1996 Fujita et al.

OTHER PUBLICATIONS

Sigma-Aldrich, "Acid Phosphatase Leukocyte (Procedure No. 387)", Revised 2003-2009, Retrieved from the internet on Sep. 20, 2010.

*Primary Examiner* — Robert Xu
(74) *Attorney, Agent, or Firm* — Sughrue Mion, PLLC

(57) ABSTRACT

The present invention relates generally to a chromogenic compositions and reagents systems and methods therefor.

**19 Claims, 1 Drawing Sheet
(1 of 1 Drawing Sheet(s) Filed in Color)**

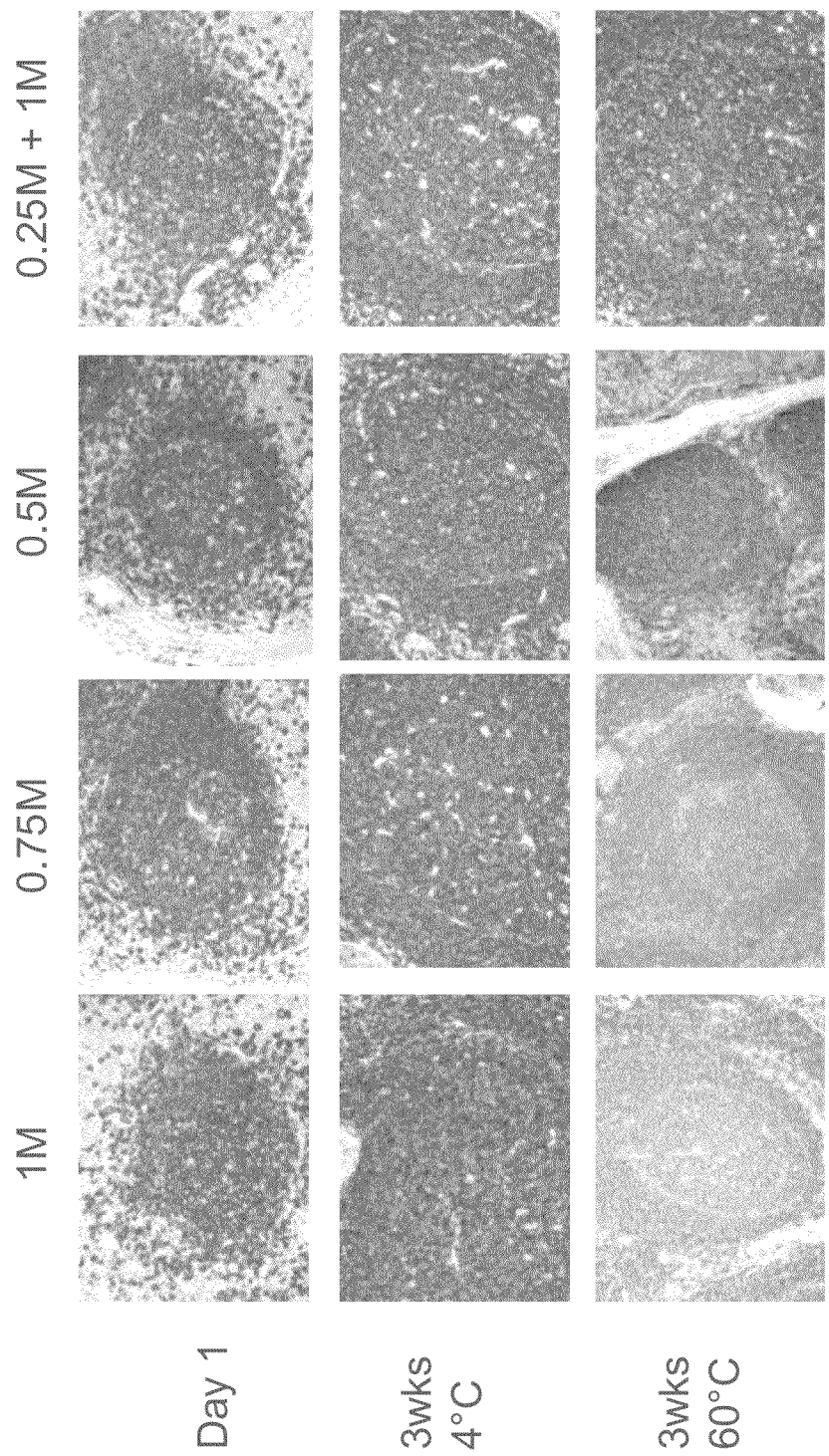

REAGENT SYSTEM AND METHOD

CROSS REFERENCE TO RELATED APPLICATIONS

This application is a National Stage of International Application No. PCT/AU2010/000956 filed Jul. 26, 2010, claiming priority based on Australian Patent Application No. 2009903535, filed Jul. 29, 2009 and U.S. Provisional Patent Application No. 61/229,644, filed Jul. 29, 2009, the contents of all of which are incorporated herein by reference in their entirety.

FIELD OF INVENTION

The present invention relates generally to chromogenic compositions and reagents systems and methods therefor. The present invention further relates to methods of preparing chromogenic compounds which are azo dyes.

BACKGROUND OF INVENTION

Chromogenic compositions comprise indicative compounds capable of producing colour by causing a displacement of, or the appearance of, absorbent bands in the visible spectrum. Chromogenic compositions have significant applications in the fields of histology, molecular biology, microbiology and the like.

Histological examination of biological samples, such as tissue samples, is commonly performed using manual or automated processes. Specialized equipment and protocols have been developed for many automated stains. There remains a need for automation of non-routine, complex or special stains. Furthermore, the increase in the use of multiple stains on a single tissue sample has required an increase in the range of stains that are distinguishable from other stains, and which can be successfully incorporated into an automated protocol.

The development of stains for both manual and automated use is often limited because of the instability of the chromogenic composition or components of the chromogenic composition, the cost of existing solutions, shelf life and storage requirements such as the need for refrigeration of some reagents.

Diazonium salts have been suggested for use in preparing chromogenic compositions. Some diazonium salts are hazardous and require careful handling when dry.

Diazonium salts are normally hygroscopic and therefore will absorb moisture from the air and become unstable if not kept in tightly sealed containers. Diazotized aromatic amines used as colorimetric indicators are also unstable in solution. While stability of these solutions can be enhanced by storage of the solution in cold and dark conditions, even under these conditions significant deterioration as evidenced by discoloration, precipitate formation, and loss of reactivity can be seen in a relatively short time.

Due to the disadvantages of using diazonium salt compounds directly, diazonium-based reagents are prepared by combining precursor reagents. However, these diazonium-based reagents are unstable and must be used within a few days or discarded.

Approaches to improve the stability of chromogenic compositions, such as diazonium-based reagents, have been modest. Accordingly, it would be very desirable to develop diazonium chromogenic compositions having even more pronounced stability.

Any discussion of documents, devices, acts or knowledge in this specification is included to explain the context of the invention. It should not be taken as an admission that any of the material formed part of the prior art base or the common general knowledge in the relevant art on or before the priority date of the invention disclosed herein or, any claims defined herein.

SUMMARY OF INVENTION

In one aspect the present invention provides a chromogenic reagent system comprising a first solution comprising a nitrite, a second solution comprising an aryl amine, a third solution comprising an acid and a fourth solution comprising a naphthol phosphate.

In a second aspect, the present invention provides a method of preparing a chromogen composition, the method comprising combining a first solution comprising a nitrite and a second solution comprising an aryl amine; to which is added a third solution comprising an acid to produce a diazonium compound;

combining said diazonium compound with a fourth solution comprising a naphthol phosphate.

One or more embodiments of the present invention may provide a composition or method which at least partially alleviates at least one disadvantage of the prior art arrangements.

In one embodiment, the nitrite is a group I or group II nitrite selected from the group consisting of sodium nitrite, potassium nitrite, lithium nitrite, calcium nitrite and magnesium nitrite, or mixtures thereof.

In one embodiment, the nitrite is sodium nitrite.

In some embodiments, the aryl amine is an aminobenzamide compound. In some embodiments the aryl amine is selected from the group comprising 3-amino-4-methoxybenzamide, 2-amino-4-methoxybenzamide, 4-aminobenzoic acid, 3-amino-4-methoxybenzoic acid, 2-aminoterephthalic acid, 2-amino-5-hydroxybenzoic acid, 2-amino-4-chlorobenzoic acid, aniline, 4-nitroanline, 2-methoxyanline, 4-chloro-2-methylaniline and 2-amino-4,5-dimethoxybenzoic acid, salts and hydrates thereof and mixtures thereof.

In one embodiment, the aryl amine is 3-amino-4-methoxybenzamide.

In one embodiment, the third solution acid is selected from the group comprising hydrochloric acid, nitric acid, perchloric acid, acetic acid, boric acid, fluoroboric acid and sulphuric acid, and mixtures thereof.

In one embodiment, the acid is hydrochloric acid.

In one embodiment, the naphthol phosphate is selected from the group comprising naphthol AS phosphate, naphthol AS-OL phosphate, naphthol AS-E phosphate, naphthol AS-MX phosphate, naphthol AS-TR phosphate and naphthol AS-BI phosphate, naphthol AS-BS phosphate, naphthol AS-GR phosphate, and salts and hydrates thereof and mixtures thereof.

In one embodiment, the naphthol phosphate is naphthol AS-TR phosphate.

In a third aspect, the present invention provides a kit for preparing a chromogenic composition, the kit comprising one or more solutions according to the first aspect of the invention, and instructions for use of the kit.

In a fourth aspect, the present invention provides a chromogenic reagent system comprising a first solution comprising nitrite, a second solution comprising an aryl amine in an acidic solution and a third solution comprising a naphthol phosphate.

In a fifth aspect, the invention provides a method of staining a biological specimen comprising:
(i) combining a first solution comprising a nitrite and a second solution comprising an aryl amine; to which is added a third solution comprising an acid to produce a diazonium compound;
combining said diazonium compound with a fourth solution comprising a naphthol phosphate to produce a chromogen composition; and
(ii) applying said chromogen composition to said biological specimen.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Other features and advantages of one or more embodiments of the present invention will be readily apparent to one of ordinary skill in the art from the following written description with reference to and, used in conjunction with, the accompanying drawings, in which:

FIG. 1 shows the staining (Leica Bond™ Advanced Staining System) for CD20 achieved when using a 40 mg/mL solution of 3-amino-4-methoxybenzamide made up using various acid concentrations, one of which is exemplified in Example 1.

DETAILED DESCRIPTION

Histological examination via immunohistochemistry (IHC) using hydrolase enzymes such as alkaline phosphatase (AP) in conjunction with naphthol phosphates and diazonium compounds is limited by the stability of the diazonium compound.

As used herein, the term "diazo compound" or "diazonium compound" means an aromatic diazonium salt formed from the reaction of a primary aryl amine and a nitrite compound. Typically, diazo compounds are compounds which have the $-+N\equiv N$ group attached to a carbon atom. Diazonium salts as referred to herein are compounds of structure RN2+ Y−, in which R is aryl.

The present invention allows for reagents systems and methods for the preparation of diazonium compounds on an as-needed basis and may provide advantages such as extended shelf-life, improved reproducibility and staining quality. The diazonium compound preparation can be automated so that it is available on an as-needed basis that avoids the short term stability issues associated with diazonium compounds.

In accordance with the present invention, one or more embodiments may provide a reagent system which is capable of forming a diazonium reagent of improved stability.

In one aspect the present invention provides a reagent system comprising a first solution comprising a nitrite, a second solution comprising an aryl amine, a third solution comprising an acid and a fourth solution comprising a naphthol phosphate.

In one embodiment, the nitrite is a group I or group II nitrite selected from the group comprising sodium nitrite, potassium nitrite, lithium nitrite, calcium nitrite and magnesium nitrite, and mixtures thereof.

In one embodiment, the nitrite is sodium nitrite.

The term "aryl amine" is intended to include salts and hydrates of aryl amine compounds.

The term "aryl" includes mono and polycyclic aromatic hydrocarbons residues such as benzene or naphthalene. In certain embodiments the aryl group is a benzene residue. The aryl group, e.g. benezene residue, may be further substituted by one or more substituents (R) wherein each R may be the same or different. In certain embodiments R is selected from $C_{1-6}$alkyl (e.g. methyl, ethylpropyl), $C_{1-6}$alkoxy (e.g. methyoxy, ethoxy and propoxy), halo (e.g. chloro, fluoro, iodo and bromo), $C(O)C_{1-6}$alkyl, OH, $CONH_2$, $CO_2H$, $NHC(O)Ph$, $NO_2$, and $SO_2NH(C_{1-6}alkyl)_2$, e.g. $SO_2NHEt_2$.

In one embodiment, the aryl amine is selected from the group comprising 3-amino-4-methoxybenzamide, 2-amino-4-methoxybenzamide, 4-aminobenzoic acid, 3-amino-4-methoxybenzoic acid, 2-aminoterephthalic acid, 2-amino-5-hydroxybenzoic acid, 2-amino-4-chlorobenzoic acid, aniline, 4-nitroanline, 2-methoxyanline, 4-chloro-2-methylaniline and 2-amino-4,5-dimethoxybenzoic acid and salts and hydrates thereof and mixtures thereof. Suitable salts include halide (i.e. chloride, bromide, iodide, fluoride) sulfates, phosphates, $BF_4^-$, zinc chloride and nitrates.

In one embodiment the aryl amine is 3-amino-4-methoxybenzamide.

In one embodiment the aryl amine is dissolved in an acid. In one embodiment the concentration of the acid is in the range of 0.2M to 0.3M. In a further embodiment the concentration of the acid is in the range of 0.22M to 0.28M. In still a further embodiment the concentration of the acid is about 0.25M.

In one embodiment the aryl amine and acid molar ratio in the second solution is about 1 to 1.

In one embodiment the aryl amine is dissolved at a concentration in the range of 38 mg/mL to 42 mg/mL. In one embodiment the aryl amine is dissolved at a concentration of about 40 mg/mL.

Without being limited by theory, the inventors have found that as the acid concentration increases above the equimolar ratio, then more degradation occurs. Accordingly, in certain embodiments the concentration of acid to aryl amine is equimolar or less.

In one embodiment, the third solution acid is selected from the group comprising hydrochloric acid, nitric acid, perchloric acid, acetic acid, boric acid, fluoroboric acid and sulphuric acid, and mixtures thereof.

In one embodiment, the acid is hydrochloric acid.

The term "naphthol phosphate" is well understood in the art and is intended to encompass anthracene-based compounds, which although do not contain a naphthol group as such, are commonly referred to as a "naphthol phosphate", such as the compound known as "naphthol-AS-GR phosphate". "Naphthol phosphate" is intended to further include salts and hydrates thereof.

In one embodiment, the naphthol phosphate is selected from the group comprising naphthol AS phosphate, naphthol AS-OL phosphate, naphthol AS-E phosphate, naphthol AS-MX phosphate, naphthol AS-TR phosphate, naphthol AS-BI phosphate, naphthol AS-BS phosphate and naphthol AS-GR phosphate, the salts and hydrates thereof and mixtures thereof.

Suitable salts include lithium, sodium, potassium, ammonium, magnesium calcium and alkylammonium salts.

In one embodiment, the naphthol phosphate is naphthol AS-TR phosphate.

In certain embodiments of the invention, the aryl amine is 3-amino-4-methyoxybenzamide, the nitrite is sodium nitrite and the naphthol phosphate is naphthol-AS-TR phosphate. In further embodiments thereof, the acid is HCl.

The chromogenic reagent systems and methods described herein may be used to produce chromogens as depicted below in Table 1:

TABLE 1

COUPLING PRODUCTS

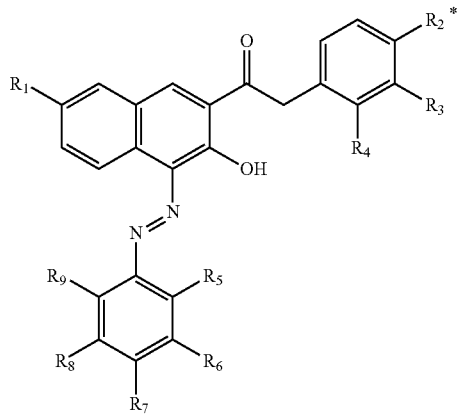

| NP | Amine | R1 | R2 | R3 | R4 | R5 | R6 | R7 | R8 | R9 |
|---|---|---|---|---|---|---|---|---|---|---|
| AS | FR-ITR | H | H | H | H | $OCH_3$ | H | $SO_2NEt_2$ | H | H |
| AS | FR-KL (3) | H | H | H | H | $OCH_3$ | H | H | $CONH_2$ | H |
| AS | PABA | H | H | H | H | H | H | $CO_2H$ | H | H |
| AS | ATA | H | H | H | H | $COCH_3$ | H | H | $COCH_3$ | H |
| AS | FR-VLB | H | H | H | H | H | Cl | NHCOPh | H | $CH_3$ |
| AS | ACB | H | H | H | H | H | Cl | H | H | $CO_2H$ |
| AS | ADB | H | H | H | H | H | $OCH_3$ | $OCH_3$ | H | H |
| AS | AMBA | H | H | H | H | $OCH_3$ | H | H | $CO_2H$ | H |
| AS | AHB | H | H | H | H | H | H | OH | $CO_2H$ | H |
| AS | FR-TR | H | H | H | H | $CH_3$ | H | Cl | H | H |
| AS | FR-KL (2) | H | H | H | H | H | $OCH_3$ | H | H | $CONH_2$ |
| AS | A | H | H | H | H | H | H | H | H | H |
| AS | FR-GG | H | H | H | H | H | H | $NO_2$ | H | H |
| AS | MBA | H | H | H | H | $OCH_3$ | H | H | H | H |
| AS | CMA | H | H | H | H | $CH_3$ | H | Cl | H | H |
| AS-OL | FR-ITR | H | H | H | $OCH_3$ | $OCH_3$ | H | $SO_2NEt_2$ | H | H |
| AS-OL | FR-KL (3) | H | H | H | $OCH_3$ | $OCH_3$ | H | H | $CONH_2$ | H |
| AS-OL | PABA | H | H | H | $OCH_3$ | H | H | $CO_2H$ | H | H |
| AS-OL | ATA | H | H | H | $OCH_3$ | $COCH_3$ | H | H | $COCH_3$ | H |
| AS-OL | FR-VLB | H | H | H | $OCH_3$ | H | Cl | NHCOPh | H | $CH_3$ |
| AS-OL | ACB | H | H | H | $OCH_3$ | H | Cl | H | H | $CO_2H$ |
| AS-OL | ADB | H | H | H | $OCH_3$ | H | $OCH_3$ | $OCH_3$ | H | H |
| AS-OL | AMBA | H | H | H | $OCH_3$ | $OCH_3$ | H | H | $CO_2H$ | H |
| AS-OL | AHB | H | H | H | $OCH_3$ | H | H | OH | $CO_2H$ | H |
| AS-OL | FR-TR | H | H | H | $OCH_3$ | $CH_3$ | H | Cl | H | H |
| AS-OL | FR-KL (2) | H | H | H | $OCH_3$ | H | $OCH_3$ | H | H | $CONH_2$ |
| AS-OL | A | H | H | H | $OCH_3$ | H | H | H | H | H |
| AS-OL | FR-GG | H | H | H | $OCH_3$ | H | H | $NO_2$ | H | H |
| AS-OL | MBA | H | H | H | $OCH_3$ | $OCH_3$ | H | H | H | H |
| AS-OL | CMA | H | H | H | H | $CH_3$ | H | Cl | H | H |
| AS-E | FR-ITR | H | Cl | H | H | $OCH_3$ | H | $SO_2NEt_2$ | H | H |
| AS-E | FR-KL (3) | H | Cl | H | H | $OCH_3$ | H | H | $CONH_2$ | H |
| AS-E | PABA | H | Cl | H | H | H | H | $CO_2H$ | H | H |
| AS-E | ATA | H | Cl | H | H | $COCH_3$ | H | H | $COCH_3$ | H |
| AS-E | FR-VLB | H | Cl | H | H | H | Cl | NHCOPh | H | $CH_3$ |
| AS-E | ACB | H | Cl | H | H | H | Cl | H | H | $CO_2H$ |
| AS-E | ADB | H | Cl | H | H | H | $OCH_3$ | $OCH_3$ | H | H |
| AS-E | AMBA | H | Cl | H | H | $OCH_3$ | H | H | $CO_2H$ | H |
| AS-E | AHB | H | Cl | H | H | H | H | OH | $CO_2H$ | H |
| AS-E | FR-TR | H | Cl | H | H | $CH_3$ | H | Cl | H | H |
| AS-E | FR-KL (2) | H | Cl | H | H | H | $OCH_3$ | H | H | $CONH_2$ |
| AS-E | A | H | Cl | H | H | H | H | H | H | H |
| AS-E | FR-GG | H | Cl | H | H | H | H | $NO_2$ | H | H |
| AS-E | MBA | H | Cl | H | H | $OCH_3$ | H | H | H | H |
| AS-E | CMA | H | Cl | H | H | $CH_3$ | H | Cl | H | H |
| AS-MX | FR-ITR | H | $CH_3$ | H | $CH_3$ | $OCH_3$ | H | $SO_2NEt_2$ | H | H |
| AS-MX | FR-KL (3) | H | $CH_3$ | H | $CH_3$ | $OCH_3$ | H | H | $CONH_2$ | H |
| AS-MX | PABA | H | $CH_3$ | H | $CH_3$ | H | H | $CO_2H$ | H | H |
| AS-MX | ATA | H | $CH_3$ | H | $CH_3$ | $COCH_3$ | H | H | $COCH_3$ | H |
| AS-MX | FR-VLB | H | $CH_3$ | H | $CH_3$ | H | Cl | NHCOPh | H | $CH_3$ |
| AS-MX | ACB | H | $CH_3$ | H | $CH_3$ | H | Cl | H | H | $CO_2H$ |
| AS-MX | ADB | H | $CH_3$ | H | $CH_3$ | H | $OCH_3$ | $OCH_3$ | H | H |
| AS-MX | AMBA | H | $CH_3$ | H | $CH_3$ | $OCH_3$ | H | H | $CO_2H$ | H |
| AS-MX | AHB | H | $CH_3$ | H | $CH_3$ | H | H | OH | $CO_2H$ | H |
| AS-MX | FR-TR | H | $CH_3$ | H | $CH_3$ | $CH_3$ | H | Cl | H | H |

TABLE 1-continued

COUPLING PRODUCTS

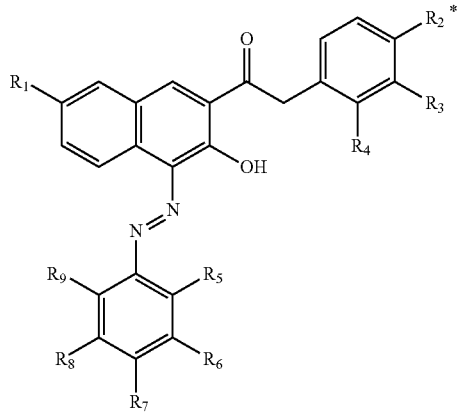

| NP | Amine | R1 | R2 | R3 | R4 | R5 | R6 | R7 | R8 | R9 |
|---|---|---|---|---|---|---|---|---|---|---|
| AS-MX | FR-KL (2) | H | $CH_3$ | H | $CH_3$ | H | $OCH_3$ | H | H | $CONH_2$ |
| AS-MX | A | H | $CH_3$ | H | $CH_3$ | H | H | H | H | H |
| AS-MX | FR-GG | H | $CH_3$ | H | $CH_3$ | H | H | $NO_2$ | H | H |
| AS-MX | MBA | H | $CH_3$ | H | $CH_3$ | $OCH_3$ | H | H | H | H |
| AS-MX | CMA | H | $CH_3$ | H | $CH_3$ | $CH_3$ | H | Cl | H | H |
| AS-TR | FR-ITR | H | Cl | H | $CH_3$ | $OCH_3$ | H | $SO_2NEt_2$ | H | H |
| AS-TR | FR-KL (3) | H | Cl | H | $CH_3$ | $OCH_3$ | H | H | $CONH_2$ | H |
| AS-TR | PABA | H | Cl | H | $CH_3$ | H | H | $CO_2H$ | H | H |
| AS-TR | ATA | H | Cl | H | $CH_3$ | $COCH_3$ | H | H | $COCH_3$ | H |
| AS-TR | FR-VLB | H | Cl | H | $CH_3$ | H | Cl | NHCOPh | H | $CH_3$ |
| AS-TR | ACB | H | Cl | H | $CH_3$ | H | Cl | H | H | $CO_2H$ |
| AS-TR | ADB | H | Cl | H | $CH_3$ | H | $OCH_3$ | $OCH_3$ | H | H |
| AS-TR | AMBA | H | Cl | H | $CH_3$ | $OCH_3$ | H | H | $CO_2H$ | H |
| AS-TR | AHB | H | Cl | H | $CH_3$ | H | H | OH | $CO_2H$ | H |
| AS-TR | FR-TR | H | Cl | H | $CH_3$ | $CH_3$ | H | Cl | H | H |
| AS-TR | FR-KL (2) | H | Cl | H | $CH_3$ | H | $OCH_3$ | H | H | $CONH_2$ |
| AS-TR | A | H | Cl | H | $CH_3$ | H | H | H | H | H |
| AS-TR | FR-GG | H | Cl | H | $CH_3$ | H | H | $NO_2$ | H | H |
| AS-TR | MBA | H | Cl | H | $CH_3$ | $OCH_3$ | H | H | H | H |
| AS-TR | CMA | H | Cl | H | $CH_3$ | $CH_3$ | H | Cl | H | H |
| AS-BI | FR-ITR | Br | H | H | $OCH_3$ | $OCH_3$ | H | $SO_2NEt_2$ | H | H |
| AS-BI | FR-KL (3) | Br | H | H | $OCH_3$ | $OCH_3$ | H | H | $CONH_2$ | H |
| AS-BI | PABA | Br | H | H | $OCH_3$ | H | H | $CO_2H$ | H | H |
| AS-BI | ATA | Br | H | H | $OCH_3$ | $COCH_3$ | H | H | $COCH_3$ | H |
| AS-BI | FR-VLB | Br | H | H | $OCH_3$ | H | Cl | NHCOPh | H | $CH_3$ |
| AS-BI | ACB | Br | H | H | $OCH_3$ | H | Cl | H | H | $CO_2H$ |
| AS-BI | ADB | Br | H | H | $OCH_3$ | H | $OCH_3$ | $OCH_3$ | H | H |
| AS-BI | AMBA | Br | H | H | $OCH_3$ | $OCH_3$ | H | H | $CO_2H$ | H |
| AS-BI | AHB | Br | H | H | $OCH_3$ | H | H | OH | $CO_2H$ | H |
| AS-BI | FR-TR | Br | H | H | $OCH_3$ | $CH_3$ | H | Cl | H | H |
| AS-BI | FR-KL (2) | Br | H | H | $OCH_3$ | H | $OCH_3$ | H | H | $CONH_2$ |
| AS-BI | A | Br | H | H | $OCH_3$ | H | H | H | H | H |
| AS-BI | FR-GG | Br | H | H | $OCH_3$ | H | H | $NO_2$ | H | H |
| AS-BI | MBA | Br | H | H | $OCH_3$ | $OCH_3$ | H | H | H | H |
| AS-BI | CMA | Br | H | H | $OCH_3$ | $CH_3$ | H | Cl | H | H |
| AS-BS | FR-ITR | H | H | $NO_2$ | H | $OCH_3$ | H | $SO_2NEt_2$ | H | H |
| AS-BS | FR-KL (3) | H | H | $NO_2$ | H | $OCH_3$ | H | H | $CONH_2$ | H |
| AS-BS | PABA | H | H | $NO_2$ | H | H | H | $CO_2H$ | H | H |
| AS-BS | ATA | H | H | $NO_2$ | H | $COCH_3$ | H | H | $COCH_3$ | H |
| AS-BS | FR-VLB | H | H | $NO_2$ | H | H | Cl | NHCOPh | H | $CH_3$ |
| AS-BS | ACB | H | H | $NO_2$ | H | H | Cl | H | H | $CO_2H$ |
| AS-BS | ADB | H | H | $NO_2$ | H | H | $OCH_3$ | $OCH_3$ | H | H |
| AS-BS | AMBA | H | H | $NO_2$ | H | $OCH_3$ | H | H | $CO_2H$ | H |
| AS-BS | AHB | H | H | $NO_2$ | H | H | H | OH | $CO_2H$ | H |
| AS-BS | FR-TR | H | H | $NO_2$ | H | $CH_3$ | H | Cl | H | H |
| AS-BS | FR-KL (2) | H | H | $NO_2$ | H | H | $OCH_3$ | H | H | $CONH_2$ |
| AS-BS | A | H | H | $NO_2$ | H | H | H | H | H | H |
| AS-BS | FR-GG | H | H | $NO_2$ | H | H | H | $NO_2$ | H | H |
| AS-BS | MBA | H | H | $NO_2$ | H | $OCH_3$ | H | H | H | H |
| AS-BS | CMA | H | H | $NO_2$ | H | $CH_3$ | H | Cl | H | H |
| AS-GR* | FR-ITR |  | H | H | $CH_3$ | $OCH_3$ | H | $SO_2NEt_2$ | H | H |
| AS-GR* | FR-KL (3) |  | H | H | $CH_3$ | $OCH_3$ | H | H | $CONH_2$ | H |
| AS-GR* | PABA |  | H | H | $CH_3$ | H | H | $CO_2H$ | H | H |
| AS-GR* | ATA |  | H | H | $CH_3$ | $COCH_3$ | H | H | $COCH_3$ | H |
| AS-GR* | FR-VLB |  | H | H | $CH_3$ | H | Cl | NHCOPh | H | $CH_3$ |

TABLE 1-continued

COUPLING PRODUCTS

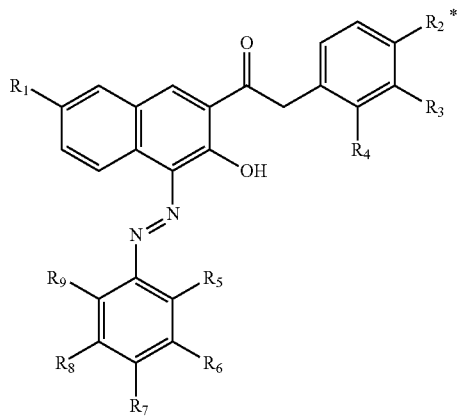

| NP | Amine | R1 | R2 | R3 | R4 | R5 | R6 | R7 | R8 | R9 |
|---|---|---|---|---|---|---|---|---|---|---|
| AS-GR* | ACB | H | H | CH$_3$ | H | Cl | H | H | CO$_2$H |
| AS-GR* | ADB | H | H | CH$_3$ | H | OCH$_3$ | OCH$_3$ | H | H |
| AS-GR* | AMBA | H | H | CH$_3$ | OCH$_3$ | H | H | CO$_2$H | H |
| AS-GR* | AHB | H | H | CH$_3$ | H | H | OH | CO$_2$H | H |
| AS-GR* | FR-TR | H | H | CH$_3$ | CH$_3$ | H | Cl | H | H |
| AS-GR* | FR-KL (2) | H | H | CH$_3$ | H | OCH$_3$ | H | H | CONH$_2$ |
| AS-GR* | A | H | H | CH$_3$ | H | H | H | H | H |
| AS-GR* | FR-GG | H | H | CH$_3$ | H | H | NO$_2$ | H | H |
| AS-GR* | MBA | H | H | CH$_3$ | OCH$_3$ | H | H | H | H |

*It will be appreciated that the C$_{10}$ naphthyl moiety of the depicted formula is replaced by the corresponding C$_{14}$ anthracene moiety of AS-GR

| | |
|---|---|
| FR-ITR | Fast red ITR (2-methoxy-5-diethylsulfonylaniline) |
| FR-KL (3) | Fast Red KL (3-amino-4-methoxybenzamide) |
| PABA | p-aminobenzoic acid |
| ATA | 2-aminoterephthalic acid |
| FR-VLB | Fast red VLB (5-chloro-4-benzamido-2-methylaniline) |
| ACB | 2-amino-4-chlorobenzoic acid |
| ADB | 2-amino-4,5-dimethoxybenzoic acid |
| AMBA | 3-amino-4-methoxybenzoic acid |
| AHB | 2-amino-5-hydroxybenzoic acid |
| FR-TR | Fast red TR (4-chloro-2-methylaniline) |
| FR-KL (2) | Fast red KL (2-amino-4-methoxybenzamide) |
| A | Aniline |
| FR-GG | Fast red GG (4-nitroaniline) |
| MBA | 2-methoxyaniline |
| CMA | 4-chloro-2-methylaniline |
| AS | N-phenyl-3-(phosphonooxy)-2-naphthalenecarboxamide |
| AS-OL | N-(2-methoxyphenyl)-3-(phosphonooxy)-2-naphthalenecarboxamide |
| AS-E | N-(4-chlorophenyl)-3-(phosphonooxy)naphthalene-2-carboxamide |
| AS-MX | N-(2,4-dimethylphenyl)-3-phosphonooxy)-2-naphthalenecarboxamide |
| AS-TR | N-(4-chloro-2-methylphenyl)-3-(phosphonooxy)-2-naphthalenecarboxamide |
| AS-BI | 7-bromo-n-(2-methoxyphenyl)-3-(phosphonooxy)-2-naphthalenecarboxamide |
| AS-BS | N-(3-nitrophenyl)-3-(phosphonooxy)-2-naphthalenecarboxamide |
| AS-GR | [3-[(2-methylphenyl)carbamoyl]anthracen-2-yl] dihydrogen phosphate |

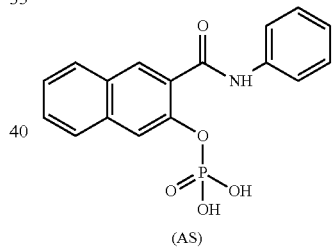

(AS)

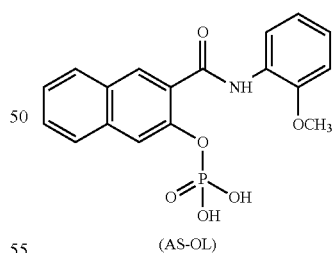

(AS-OL)

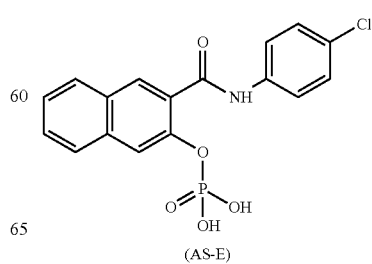

(AS-E)

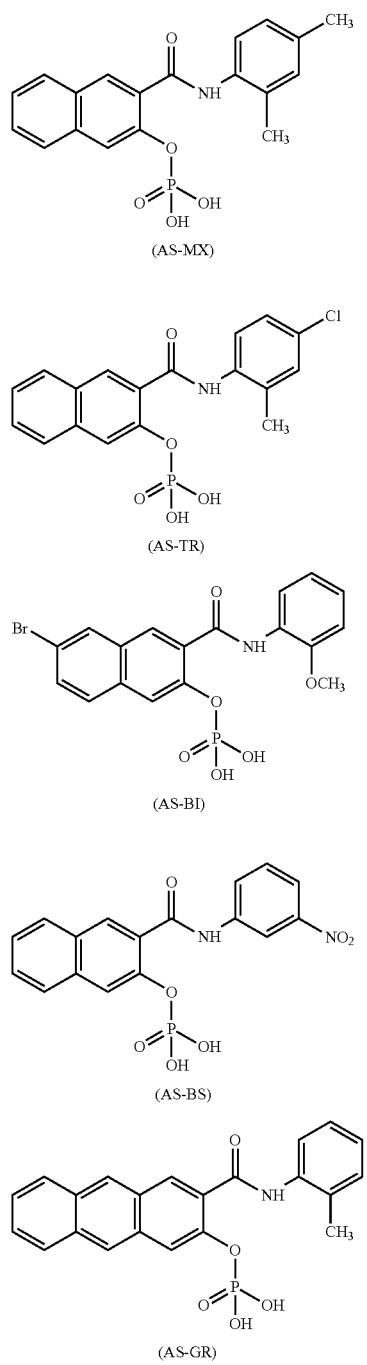

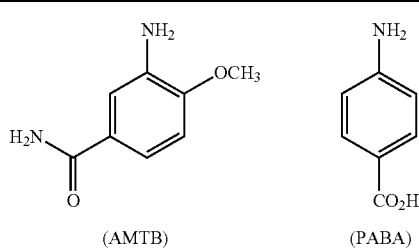

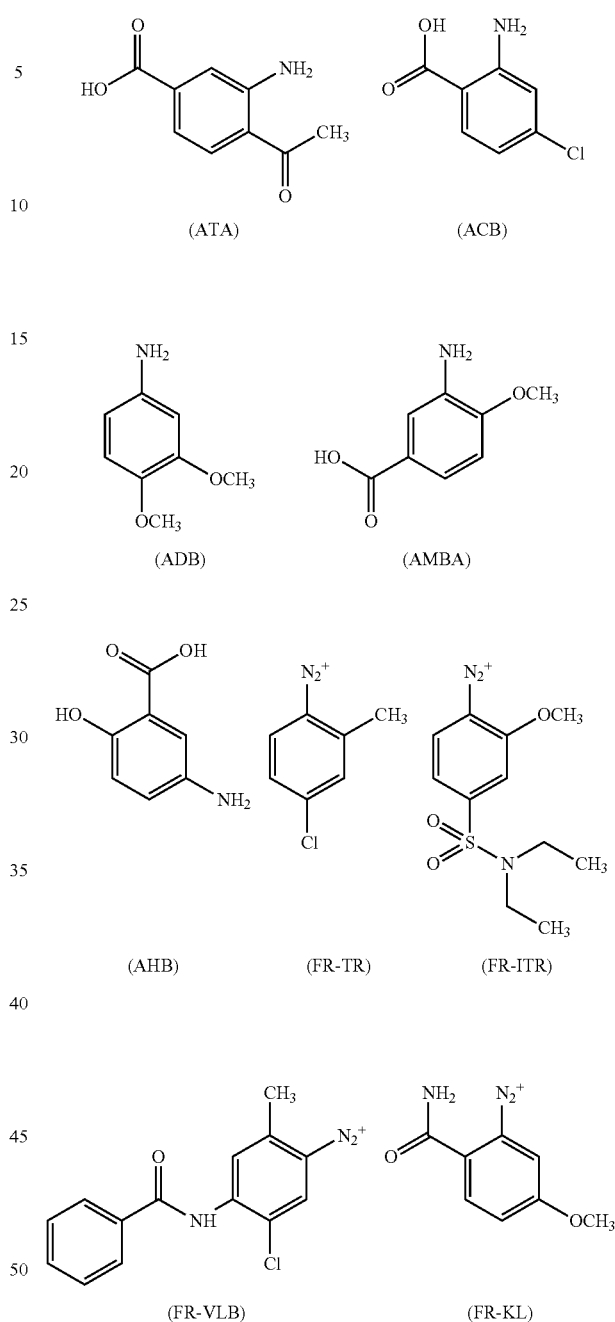

(FR-ITR) 2-Methoxy-5-(diethylaminosulfonyl) diazonium ion (Fast Red ITR)
(FR-TR) 4-Chloro-2-methylbenzene diazonium ion (Fast Red TR)
(FR-VLB) 5-Chloro-4-benzamido-2-methylbenzenediazonium ion (Fast Red VLB)
(FR-KL) 2-Carbamoyl-5-methoxybenzenediazonium ion (Fast Red KL)
(AMTB) 3-Amino-4-methoxybenzamide
(PABA) p-Aminobenzoic acid
(AMBA) 3-amino-4-methoxybenzoic acid
(ATA) 2-aminoterephthalic acid
(AHB) 2-amino-5-hydroxybenzoic acid
(ACB) 2-amino-4-chlorobenzoic acid
(ADB) 2-amino-4,5-dimethoxybenzoic acid

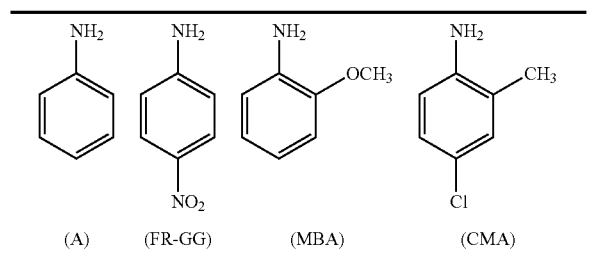

(FR-GG) 4-Nitroaniline (Fast Red GG)
(MBA) 2-Methoxyaniline
(A) Aniline
(CMA) 4-Chloro-2-methylaniline In one embodiment, the naphthol phosphate solution is buffered to pH 8 to 9. In a further embodiment the naphthol phosphate solution is buffered to pH 8.7 to 8.9. In still a further embodiment the naphthol phosphate solution is buffered to about pH 8.8.

In one embodiment, nitrite to aryl amine to naphthol phosphate is a 1 to 1 to 1 molar ratio.

In a second aspect, the present invention provides a method of preparing a chromogen composition, the method comprising combining a first solution comprising a nitrite and a second solution comprising an aryl amine; to which is added a third solution comprising an acid to produce a diazonium compound;

combining said diazonium compound with a fourth solution comprising a naphthol phosphate.

A generalised scheme is presented below:

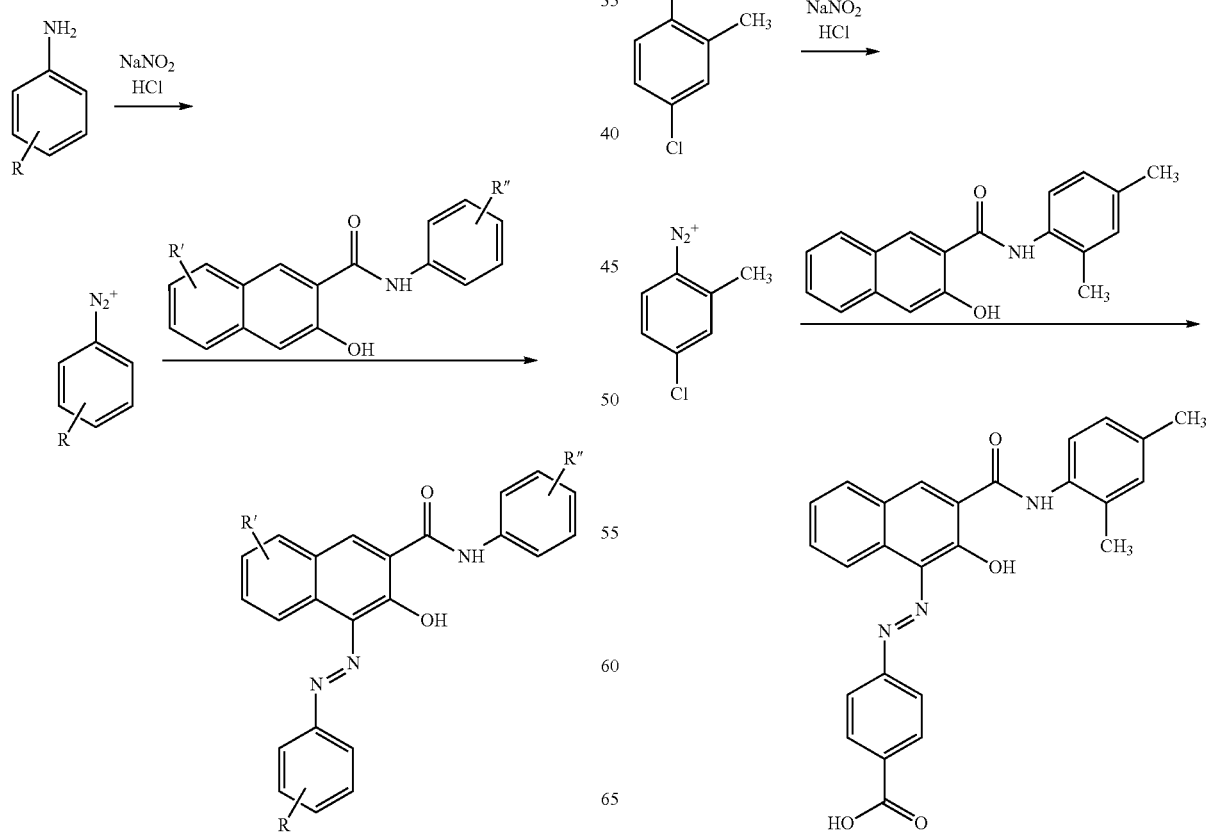

Some specific examples are further depicted below

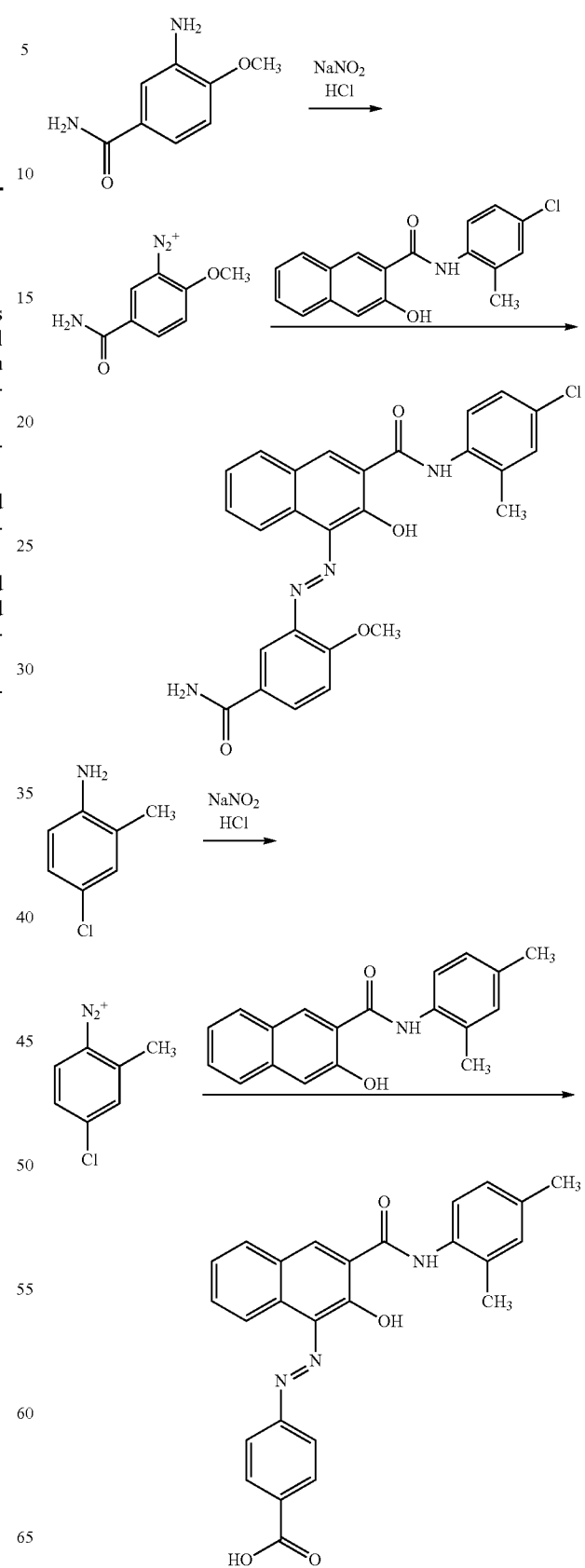

In one embodiment, the nitrite solution is added to the aryl amine solution. In another embodiment, the aryl amine solution is added to the nitrite solution.

Phosphatases typically operate by hydrolyzing a substrate which is a phosphate ester of a substituted naphthol or anthracenol, e.g., naphthol AS phosphate (N-phenyl-3-(phosphonooxy)naphthalene-2-carboxamide). The free naphthol then reacts with a stable soluble diazotate in the developing solution, e.g, Fast Red KL, Fast Red TR or Fast Red Violet LB, forming an insoluble dye.

In certain embodiments of the invention, naphthol phosphate solution contains sodium chloride and magnesium chloride to assist in the alkaline phosphatase (AP) reaction.

In one embodiment, for tissue staining, levamisole is added to block endogenous AP in the tissue.

In one embodiment a preservative such as ProClin™ 950 is included as part of one of the first to fourth solutions, or added as part of a final solution.

The chromogenic compositions produced according to the methods of the present invention may be used for staining biological specimens including, but not limited to, tissue sections, cell cultures, smears, aspirates and others. In one embodiment, the biological specimen is a tissue section suitable for histological staining, such as immunohistochemical analysis or in situ hybridization.

Accordingly, the invention further provides a method of staining a biological specimen, comprising:
(i) combining a first solution comprising a nitrite and a second solution comprising an aryl amine; to which is added a third solution comprising an acid to produce a diazonium compound;
combining said diazonium compound with a fourth solution comprising a naphthol phosphate to produce a chromogen composition; and
(ii) applying said chromogen composition to said biological specimen.

In one embodiment, by using a solution of an aryl amine and mixing this with an aqueous nitrite solution and an acid, the diazonium is prepared in small amounts on an as-needed basis, using an automated platform such as a robotic staining instrument (e.g. Leica's Bond™ Advanced Staining System).

The present invention may advantageously reduce the need to attempt to stabilise an unstable group of compounds. It limits the use of solid formulations and the need for low temperature refrigeration.

Advantageously, this may allow a formulation that results in a substantial increase in the shelf life of the chromogenic system.

In certain embodiments, the chromogen composition prepared is applied to a biological specimen within 30 minutes or less of the preparation of the diazonium compound.

The reagent systems and methods of the present invention are particularly suitable for automated staining and can be incorporated into a number of automated staining protocols. The methods of the present invention can be used in conjunction with a number of automated staining instruments and software known in the art.

Using the fluidic capabilities of the automated platform such as the Bond™ staining instrument, the necessary diazonium compound is prepared as needed, reducing the need to package it in solution, which requires stabilization and/or refrigeration. This significantly reduces the cost of the reagents and substantially prolongs the lifetime of these reagents.

Generally, each solution is delivered in amounts selected to result in a desired concentration. In one embodiment, each solution is added in a specified sequence. In one embodiment, each solution is added at the same time.

Conditions such as solvent systems, pH, temperature and others can be selected based on the particular reaction(s) chemistry known in the art.

In one embodiment, reagent system according to the present invention is suitable for use in a biotin-free, polymeric alkaline phosphatase-linked antibody conjugate system for the detection of tissue-bound mouse and rabbit IgG and some mouse IgM primary antibodies.

In one embodiment, the reagent system and methods of the present invention may be used for staining sections of formalin-fixed, paraffin-embedded tissue on the Bond™ automated staining system.

In one embodiment, the reagent system is supplied ready-to-use for the automated staining systems.

In one embodiment, the chromogenic composition produced according to the present invention comprises a diazonium compound that gives a colour that contrasts with brown, especially useful for tissues such as skin where tissue pigments can be mistaken for the DAB chromogen of a peroxidase system.

Chromogenic compositions are useful with regard to locating a protein or a specific sequence of DNA or RNA. In particular, specific sequences of DNA or RNA may be located on chromosomes or other genetic material with the use of nucleic acid probes. Nucleic acid probes contain short segments of nucleic acids which are complimentary to the specific DNA or RNA sequence to be located.

In one embodiment of the present invention, chromogenic compounds may be used to detect nucleic acid probes. Nucleic acid probes, used to locate specific DNA or RNA sequences, may contain covalently linked enzymes having specificity for a chromogenic composition of the present invention.

Chromogenic compositions produced according to the present invention are useful when used in conjunction with enzyme-antibody conjugates. Enzyme-antibody conjugates are important with respect to a range of assays such as immunohistochemical analysis of tissue samples, in situ hybridization assays and enzyme linked immunosorbent assays. In this regard, enzymes are conjugated with antigen specific antibodies which permit detection of a particular antigen. In a similar application, chromogenic compositions of the present invention may be used to detect nucleic acid probes having an enzyme complex that releases free phenols. The presence of an enzyme with the requisite specificity linked to the nucleic acid probe enables detection by a chromogenic compound of the present invention.

In the immunoalkaline phosphatase staining method, the enzyme hydrolyzes naphthol phosphate esters to phenolic compounds and phosphates. The phenols couple to colorless diazonium compounds to produce insoluble, colored azo dyes.

In some embodiments of the invention, the aryl amine and nitrite solutions can be used to prepare diazo compounds such as Fast Red KL, Fast Red TR, Fast Red ITR, Fast Red B, Fast Blue BB, and Fast Red Violet LB.

The methods of the present invention can be performed over a wide temperature range. In one embodiment, the methods can be performed at between about 0° C. to about 90° C. In one embodiment, the methods can be performed at between about 0° C. to about 50° C. In one embodiment, the methods can be performed at about 15° C. to about 30° C. In one embodiment, the methods are performed at ambient temperature.

In a third aspect, the present invention provides a kit for preparing a chromogenic solution, the kit comprising one or more solutions according to the first aspect of the invention, and instructions for use of the kit.

In a fourth aspect, the present invention provides a chromogenic reagent system comprising a first solution comprising nitrite, a second solution comprising an aryl amine in an acidic solution and a third solution comprising a naphthol phosphate.

As the present invention may be embodied in several forms without departing from the spirit of the essential characteristics of the invention, it should be understood that the above described embodiments are not to limit the present invention unless otherwise specified, but rather should be construed broadly within the spirit and scope of the present invention as defined in the appended claims. Various modifications and equivalent arrangements are intended to be included within the spirit and scope of the present invention and appended claims.

"Comprises/comprising" when used in this specification is taken to specify the presence of stated features, integers, steps or components but does not preclude the presence or addition of one or more other features, integers, steps, components or groups thereof."

EXAMPLES

Example 1

One part of a 3-amino-4-methoxybenzamide solution (40 mg/mL dissolved in 0.25M hydrochloric acid) is added to eight parts of an aqueous solution of sodium nitrite (2.05 mg/mL), then one part of a 1M hydrochloric acid solution is added and the resulting solution mixed. After five to ten minutes, 2-methoxy-5-carboxamidobenzenediazonium is formed in solution. 60 parts of a naphthol phosphate buffer (1.6 mg/mL naphthol AS-TR phosphate disodium salt in a solution of 0.1 M sodium chloride, 0.1 M magnesium chloride, 0.1 M Tris buffer, 1 mM levamisole and 0.5% ProClin™ 950 adjusted to pH 8.8) are then added and the solution briefly mixed. This mixing can be performed manually or on an automated system such as a Leica Bond™ advanced staining system.

Example 2

FIG. 1 shows tissue stained with a CD20 antibody clone on a Leica Bond™ Advanced Staining System where the chromogen has been prepared using solutions of 3-amino-4-methoxybenzamide made up using various hydrochloric acid concentrations and tissue stained as described in Example 3.

For a mixed chromogen solution using 3-amino-4-methoxybenzamide solution (40 mg/mL in 1M HCl—sodium nitrite and napthol phosphate prepared as described in Example 1), the staining is red immediately after mixing, after one day and after three weeks after having being stored at 4° C. However, after the 3-amino-4-methoxybenzamide solution has been stored for three weeks at 60° C., the histological staining is orange.

When a 40 mg/mL solution of 3-amino-4-methoxybenzamide is made up in a 0.75M HCl solution, the resultant staining is red at day one and after three weeks after having being stored at 4° C. However, after one week at 60° C., the histological staining is red-orange.

When a 40 mg/mL solution of 3-amino-4-methoxybenzamide is made up in a 0.5M HCl solution, the staining is red at day one and after three weeks after having being stored at 4° C. However, after one week at 60° C., the histological staining is a red orange.

In contrast, when a 40 mg/mL solution of 3-amino-4-methoxybenzamide is made up in a 0.25M HCl solution and a further one part 1M HCl solution added prior to use, the staining is red at day one, after three weeks after having being stored at 4° C., and after three weeks at 60° C.

The stability of the solution becomes greater as evidenced by the observed decreased orange staining as the concentration of the HCl is decreased from 1M to 0.5M, after the solution has been at 60° C. for a period of time.

The acid is required to assist the conversion of the amine to the diazonium, but it also initiates with the degradation of the 3-amino-4-methoxybenzamide to the corresponding carboxylic acid which produces the orange staining. In order to minimise the conversion to the carboxylic acid, the 3-amino-4-methoxybenzamide is dissolved in 0.25M HCl. After three weeks storage at 60° C., the solution provides acceptable red staining on tissue.

The degradation of 3-amino-4-methoxybenzamide in dilute hydrochloric acid proceeds via acid-catalysed hydrolysis of the amide to the corresponding carboxylic acid. While this acid also undergoes coupling with a naphthol, the diazonium dye formed has a different colour to that of the amide (orange not fuchsia, see scheme 1). As 3-amino-4-methoxybenzamide degrades forming more 3-amino-4-methoxybenzoic acid, the staining colour shifts from fuchsia to brick-red and finally to an orange-brown. Typically, the colour of the tissue staining moves from red to orange when the concentration of the carboxylic acid is about 10-50%.

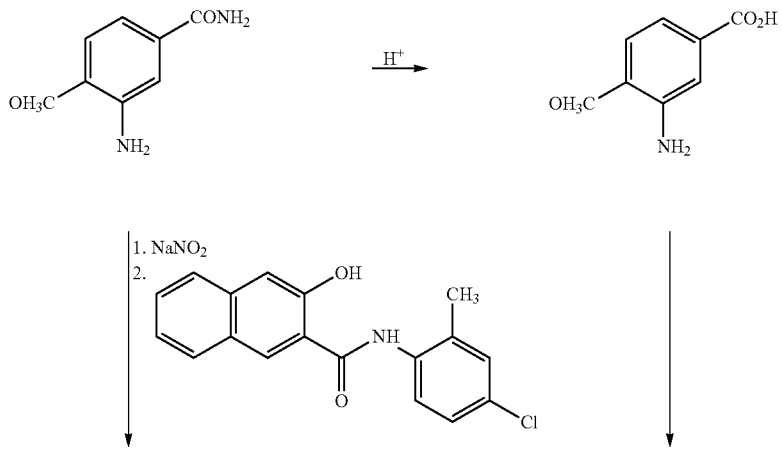

Scheme 1

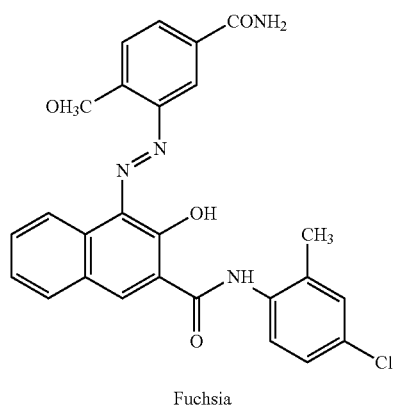

Fuchsia

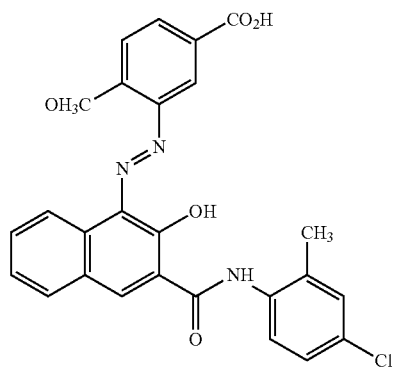

Orange

Example 3

The 3-amino-4-methoxybenzamide reacts with sodium nitrite in the presence of hydrochloric acid (as described in Example 1, and shown in Scheme 2) to form the diazonium compound in solution.

Scheme 2. Diazotisation of an amine

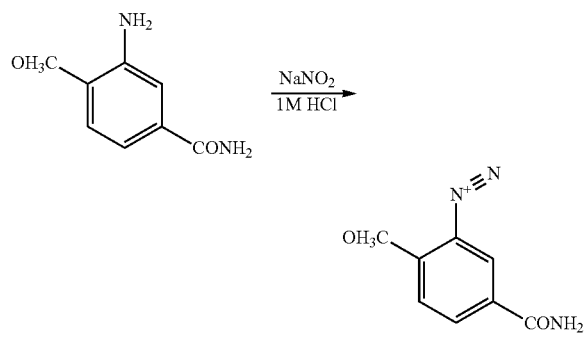

A solution containing naphthol AS-TR phosphate is then added to the solution containing the diazonium solution and this mixture is added to the tissue that has been pretreated with AP (Alkaline phosphatase) polymer. This antibody-polymer binds to tissue antigens leaving alkaline phosphatase available to react in the next step.

The mixture containing diazonium compound and the naphthol phosphate is applied to the tissue. The alkaline phosphatase enzyme bound to the tissue antigens hydrolyses the phosphate group of the naphthol phosphate forming a free naphthol (scheme 3). The reaction is facilitated by the presence of sodium chloride and magnesium chloride, an AP co-factor. The use of Trizma as a buffer is also known to enhance this enzyme reaction. The naphthol is now able to react with the diazonium compound in the next step.

Scheme 3. AP hydrolysis of naphthol phosphate

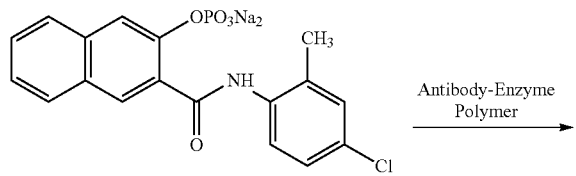

At the high pH of the buffer solution, the coupling of the naphthol to the diazonium compound occurs quickly. This forms the fuchsia coloured chromogen.

Scheme 3. Azo coupling of naphthol and diazonium compound.

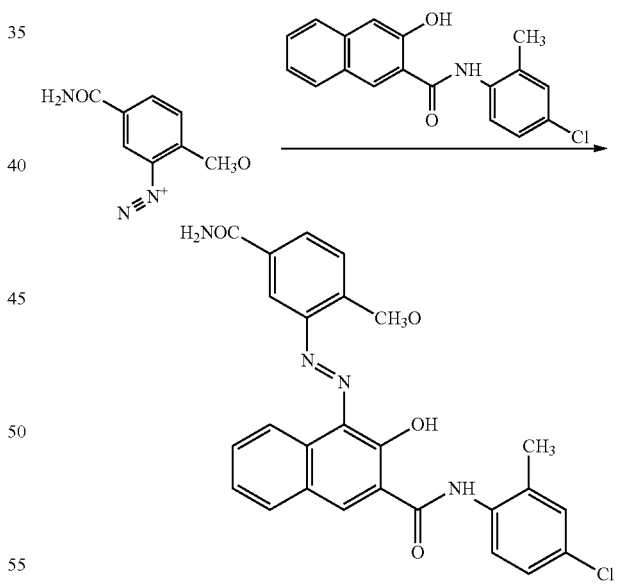

The invention claimed is:

1. A chromogenic reagent system comprising a first solution comprising a nitrite, a second solution comprising an aryl amine selected from the group comprising 3-amino-4-methoxybenzamide, 2-amino-4-methoxybenzamide, 4-aminobenzoic acid, 3-amino-4-methoxybenzoic acid, 2-aminoterephthalic acid, 2-amino-5-hydroxybenzoic acid, 2-amino-4-chlorobenzoic acid, 2-amino-4,5-dimethoxybenzoic acid aniline, 4-nitroanline, 2-methoxyanline, 4-chloro-2-methylaniline and mixtures thereof, a third solution comprising an acid and a fourth solution comprising a naphthol phosphate.

2. A method of preparing a chromogen composition, the method comprising:
combining a first solution comprising a nitrite and a second solution comprising an aryl amine selected from the group comprising 3-amino-4-methoxybenzamide, 2-amino-4-methoxybenzamide, 4-aminobenzoic acid, 3-amino-4-methoxybenzoic acid, 2-aminoterephthalic acid, 2-amino-5-hydroxybenzoic acid, 2-amino-4-chlorobenzoic acid, 2-amino-4,5-dimethoxybenzoic acid, aniline, 4-nitroanline, 2-methoxyanline, 4-chloro-2-methylaniline and mixtures thereof; to which is added a third solution comprising an acid to produce a diazonium compound; and
combining said diazonium compound with a fourth solution comprising a naphthol phosphate.

3. The reagent system according to claim 1 wherein the naphthol phosphate is selected from the group comprising naphthol AS phosphate, naphthol AS-OL phosphate, naphthol AS-E phosphate, naphthol AS-MX phosphate, naphthol AS-TR phosphate naphthol AS-BI phosphate, naphthol AS-BS phosphate and naphthol AS-GR phosphate, salts and hydrates thereof and mixtures thereof.

4. The reagent system according to claim 1 wherein the aryl amine is dissolved in an acid.

5. The reagent system according to claim 1 wherein the nitrite is selected from the group comprising sodium nitrite, potassium nitrite, lithium nitrite, calcium nitrite and magnesium nitrite, or mixtures thereof.

6. The reagent system according to claim 1 wherein the acid is selected from the group comprising hydrochloric acid, nitric acid, perchloric acid, acetic acid, boric acid, fluoroboric acid, and sulphuric acid, or mixtures thereof.

7. A kit for preparing a chromogenic solution, the kit comprising the first, second, third and fourth solutions according to claim 1, and instructions for use of the kit.

8. A reagent system comprising a first solution comprising a nitrite, a second solution comprising 3-amino-4-methoxybenzamide in an acidic solution and a third solution comprising a naphthol phosphate.

9. A method of staining a biological specimen, comprising:
(i) combining a first solution comprising a nitrite and a second solution comprising an aryl amine selected from the group comprising 3-amino-4-methoxybenzamide, 2-amino-4-methoxybenzamide, 4-aminobenzoic acid, 3-amino-4-methoxybenzoic acid, 2-aminoterephthalic acid, 2-amino-5-hydroxybenzoic acid, 2-amino-4-chlorobenzoic acid, 2-amino-4,5-dimethoxybenzoic acid, aniline, 4-nitroanline, 2-methoxyanline, 4-chloro-2-methylaniline and mixtures thereof; to which is added a third solution comprising an acid to produce a diazonium compound;
combining said diazonium compound with a fourth solution comprising a naphthol phosphate to produce a chromogen composition; and
(ii) applying said chromogen composition to said biological specimen.

10. The method of claim 9 wherein the chromogen composition is mixed on board an automated staining instrument.

11. The reagent system according to claim 1 wherein the arylamine is 3-amino-4-methoxybenzamide.

12. A chromogenic reagent system comprising a first solution comprising a nitrite, a second solution comprising 3-amino-4-methoxybenzamide in an acidic solution, wherein the molar ratio of acid to 3-amino-4-methoxybenzamide is about 1:1 or less; a third solution comprising an acid and a fourth solution comprising a naphthol phosphate.

13. The reagent system according to claim 12 wherein the 3-amino-4-methoxybenzamide is dissolved in the acidic solution at a concentration in the range of 38 mg/mL to 42 mg/mL.

14. The reagent system according to claim 13 wherein the 3-amino-4-methoxybenzamide is dissolved in the acidic solution at a concentration of about 40 mg/mL.

15. The reagent system according to claim 12 wherein the concentration of the acidic solution comprising 3-amino-4-methoxybenzamide is in the range of 0.20M to 0.30M.

16. The reagent system according to claim 15 wherein the concentration of the acidic solution comprising 3-amino-4-methoxybenzamide is in the range of 0.22M to 0.28M.

17. The reagent system according to claim 16 wherein the concentration of the acidic solution comprising 3-amino-4-methoxybenzamide is about 0.25M.

18. The reagent system according to claim 1 comprising:
a first solution comprising a nitrite;
a second solution comprising 3-amino-4-methoxybenzamide in an acidic solution;
wherein the molar ratio of acid to 3-amino-4-methoxybenzamide is about 1:1 or less;
a third solution comprising HCl; and
a fourth solution comprising a naphthol AS-TR phosphate.

19. The reagent system according to claim 1 comprising:
a first solution comprising 2.05 mg/mL sodium nitrite;
a second solution comprising 40 mg/mL 3-amino-4-methoxybenzamide in 0.25M HCl;
a third solution comprising 1M HCl; and
a fourth solution comprising 1.66 mg/mL naphthol-AS-TR phosphate disodium salt.

* * * * *